(12) United States Patent
Fukazawa et al.

(10) Patent No.: US 7,298,471 B2
(45) Date of Patent: Nov. 20, 2007

(54) SURFACE INSPECTION APPARATUS AND SURFACE INSPECTION METHOD

(75) Inventors: Kazuhiko Fukazawa, Misato (JP); Koichiro Komatsu, Tokyo (JP); Takeo Oomori, Sagamihara (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 11/410,944

(22) Filed: Apr. 26, 2006

(65) Prior Publication Data

US 2006/0192953 A1 Aug. 31, 2006

Related U.S. Application Data

(63) Continuation of application No. PCT/JP2004/015925, filed on Oct. 27, 2004.

(30) Foreign Application Priority Data

Oct. 27, 2003 (JP) ............................. 2003-366255

(51) Int. Cl.
*G01N 21/00* (2006.01)
(52) U.S. Cl. ................. 356/237.5; 356/237.2
(58) Field of Classification Search ...................... None
See application file for complete search history.

(56) References Cited

U.S. PATENT DOCUMENTS 5,046,847 A 9/1991 Nakata et al.
5,777,744 A 7/1998 Yoshii et al.
5,835,220 A * 11/1998 Kazama et al. ............. 356/369
6,594,012 B2 7/2003 Takeuchi et al.
2001/0010363 A1 8/2001 Watanabe et al.
2001/0013935 A1 8/2001 Watanabe et al.
2001/0026365 A1* 10/2001 Hirosawa ................... 356/369

FOREIGN PATENT DOCUMENTS

| JP | A 1-117024 | 5/1989 |
|---|---|---|
| JP | A 2-12002 | 1/1990 |
| JP | A 6-3278 | 1/1994 |
| JP | A 10-232122 | 9/1998 |
| JP | A 11-295231 | 10/1999 |
| JP | A 2002-116011 | 4/2002 |

* cited by examiner

*Primary Examiner*—Michael P. Stafira
(74) *Attorney, Agent, or Firm*—Oliff & Berridge PLC

(57) ABSTRACT

A surface inspection apparatus and a surface inspection method aim to securely deal with finer repetition pitch without shortening the wavelength of illumination light. To this end, the apparatus includes a unit illuminating repetitive pattern(s) formed on the substrate surface to be inspected with linearly polarized light, a unit setting to an oblique angle an angle between the direction of an intersecting line of a vibration plane of the linearly polarized light on the substrate surface and the repetition direction of repetitive pattern(s), a unit extracting a polarized light component perpendicular to the vibration plane of the linearly polarized light, from light having been emitted from the repetitive pattern(s) in a specular direction, and a unit detecting a defect of the repetitive pattern(s) according to the light intensity of the polarized light component.

14 Claims, 11 Drawing Sheets

SURFACE INSPECTION APPARATUS AND SURFACE INSPECTION METHOD

CROSS REFERENCE TO RELATED APPLICATION

This application is a continuation application of International Application PCT/JP 2004/015925, filed on Oct. 27, 2004, and claims the benefit of priority from Japanese Patent Application No. 2003-366255, filed on Oct. 27, 2003, designating the U.S.

FIELD OF THE INVENTION

The present invention relates to a surface inspection apparatus and a surface inspection method for the surface of a semiconductor wafer or a liquid crystal substrate.

DESCRIPTION OF THE RELATED ART

In the production process of a semiconductor circuit device and a liquid crystal display device, a defect inspection is performed on a repetitive pattern (pattern of lines and space such as an interconnection pattern) formed on the surface of a semiconductor wafer or a liquid crystal substrate (generally referred to as a substrate). An automated surface inspection apparatus has a substrate mounted on a tiltable stage, irradiates the surface of the substrate with illumination light (unpolarized light) for inspection, to capture the image of the substrate according to the diffracted light (for example, the first order diffracted light) that is emitted from the repetitive pattern on the substrate, and identify a defective portion of the repetitive pattern based on the contrast of the image (for example, refer to Japanese Unexamined Patent Application Publication No. 10-232122). Further, it is also possible for the conventional surface inspection apparatus to perform a defect inspection of repetitive pattern on a substrate, the repetitive pitch of which is different, by adjusting the tilt of a stage.

However, with the above-mentioned conventional surface inspection apparatus, in principle, when the pitch of repetitive pattern is less than a predetermined value (=(diffraction order)×(wavelength of illumination light)÷2), the diffracted light is not emitted from the repetitive pattern, therefore, a defect inspection cannot be performed. Further, if the repetitive pitch is in the vicinity of the predetermined value, it is difficult to realize a defect inspection with diffracted light by the restriction of the mechanical arrangement of an illumination system and a light detecting system in an apparatus.

There is one way to deal with finer repetition pitch (that is, reduction of the lines and space of such as ab interconnection pattern), and that is to reduce the above-mentioned predetermined value by shortening the wavelength of the illumination light. However, this is not preferable because it leads to limiting the kinds of light source to bulky and expensive ones as well as limiting the material for optical elements constituting the illumination system or the light detecting system to expensive ones.

SUMMARY OF THE INVENTION

An object of the present invention is to provide a surface inspection apparatus and a surface inspection method for securely dealing with finer repetitive pitch without the need to reduce the wavelength of illumination light.

A surface inspection apparatus of the present invention includes an illumination unit which illuminates with linearly polarized light repetitive pattern(s) formed on the surface of a substrate to be inspected, a setting unit which sets, to an oblique angle, an angle between a direction of a vibration plane of the linearly polarized light on the substrate surface and a repetition direction of the repetitive pattern(s), and an extraction unit which extracts a polarized light component from light that has been emitted from the repetitive pattern(s) in a specular direction. The polarized light component is perpendicular to the vibration plane of the linearly polarized light It is preferable that the surface inspection apparatus include a detection unit which detects a defect of the repetitive pattern(s) according to a light intensity of the polarized light component extracted by the extraction unit.

It is also preferable that the surface inspection apparatus include an image formation unit which forms an image of the substrate to be inspected, using the light extracted by the extraction unit and a detection unit which detects a defect of the repetitive pattern(s).

It is also preferable that the setting unit set the angle to an arbitrary value between 30 degrees and 60 degrees.

It is also preferable that the setting unit set the angle to 45 degrees.

It is also preferable that the surface inspection apparatus include a substrate support unit which supports the substrate to be inspected and rotates, within the surface, the repetition direction of the repetitive pattern(s), and that the detection unit detect a defect of the repetitive pattern(s) according to a state in which the substrate is before and after the substrate support unit rotates the repetition direction by 180 degrees.

Further, the surface inspection method of the present invention includes the steps of illuminating, with linearly polarized light, repetitive pattern(s) formed on the substrate surface to be inspected in a state in which a direction of a vibration plane of the linearly polarized light on the substrate is inclined with respect to a repetition direction of the repetitive pattern(s), and detecting a defect of the repetitive pattern(s) according to a light intensity of a polarized light component from the light that has been emitted from the repetitive pattern(s) in the specular direction, the polarized light component being perpendicular to the vibration plane of the linearly polarized light.

It is preferable that the method include the steps of illuminating, with linearly polarized light, repetitive pattern(s) formed on a surface of a substrate to be inspected in a state in which a direction of a vibration plane of the linearly polarized light on the surface is inclined with respect to a repetition direction of the repetitive pattern(s), extracting a polarized light component perpendicular to the vibration plane from light that has been emitted from the repetitive pattern(s) in the specular direction, forming an image of the substrate to be inspected using extracted light, and detecting a defect of the repetitive pattern(s) according to the formed image.

It is also preferable that the direction of the vibration plane of the linearly polarized light on the substrate surface be inclined at an arbitrary angle between 30 degrees and 60 degrees with respect to a repetition direction of the repetitive pattern(s).

It is also preferable that the direction of the vibration plane of the linearly polarized light on the substrate surface be inclined at 45 degrees with respect to the repetition direction of the repetitive pattern(s).

It is also preferable that a defect of the repetitive pattern(s) be detected in a state in which the substrate to be inspected is in before and after the repetition direction of the repetitive pattern(s) is rotated by 180 degrees within the surface.

BRIEF DESCRIPTION OF THE DRAWINGS

The nature, principle, and utility of the invention will become more apparent from the following detailed description when read in conjunction with the accompanying drawings in which like parts are designated by identical reference numbers, in which.

DESCRIPTION OF THE PREFERRED EMBODIMENT

Embodiments of the present invention are described below in detail with reference to drawings.

First Embodiment

Figure 1:
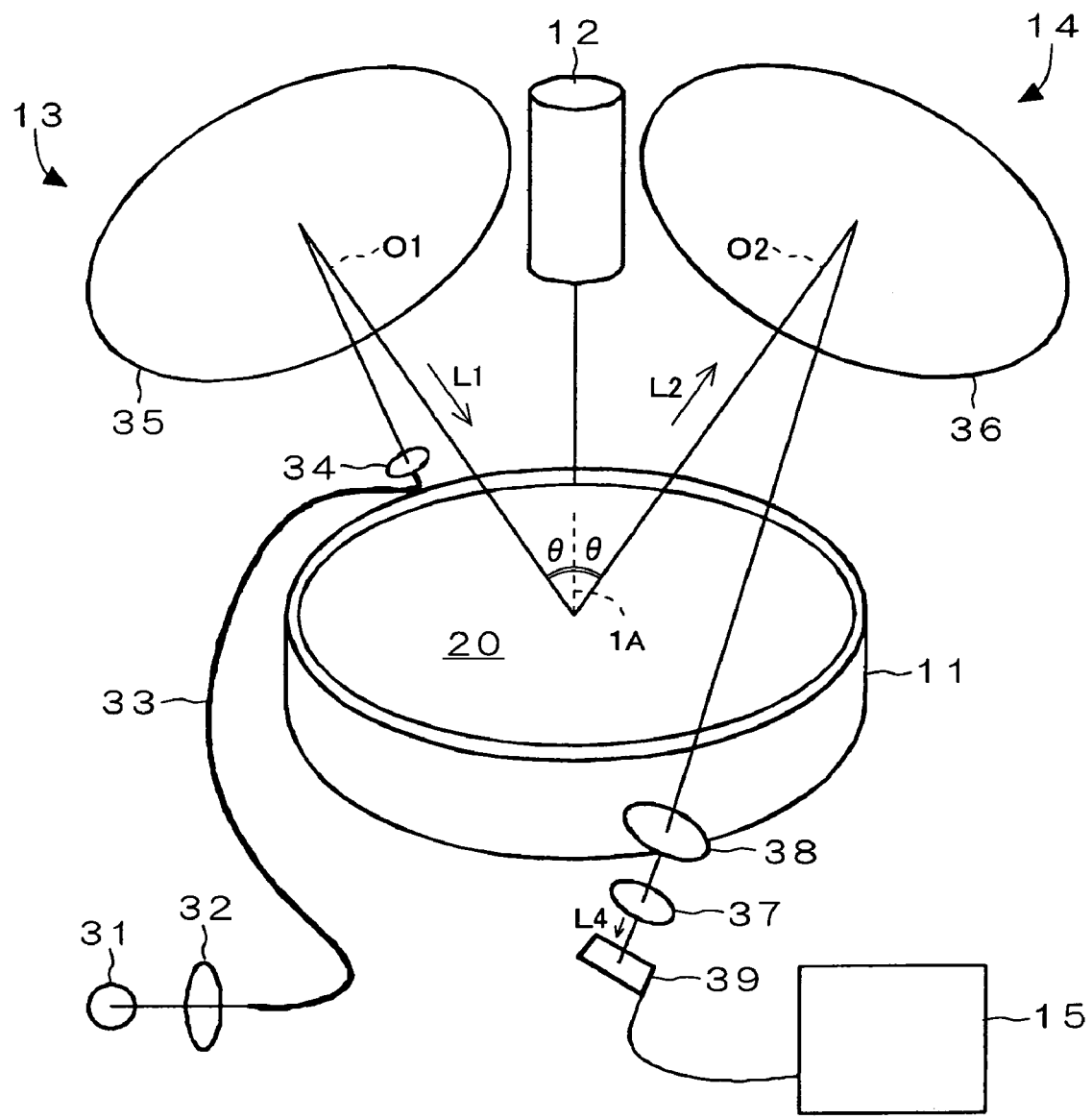
FIG. 1 shows an entire configuration of a surface inspection apparatus 10 in a first embodiment.

A surface inspection apparatus 10 in a first embodiment includes, as shown in FIG. 1, a stage 11 that supports a semiconductor wafer 20 which is a substrate to be inspected, an alignment system 12, an illumination system 13, a light detecting system 14, and an image processing device 15. The surface inspection apparatus 10 is an apparatus that automatically performs inspection of the surface of the semiconductor wafer 20 during the production process of a semiconductor circuit element. After the resist film on the uppermost layer is exposed and developed, the semiconductor wafer 20 is conveyed from a wafer cassette or a development apparatus, not shown, by a conveyer system, also not shown, and adsorbed to the stage 11.

Figure 2:
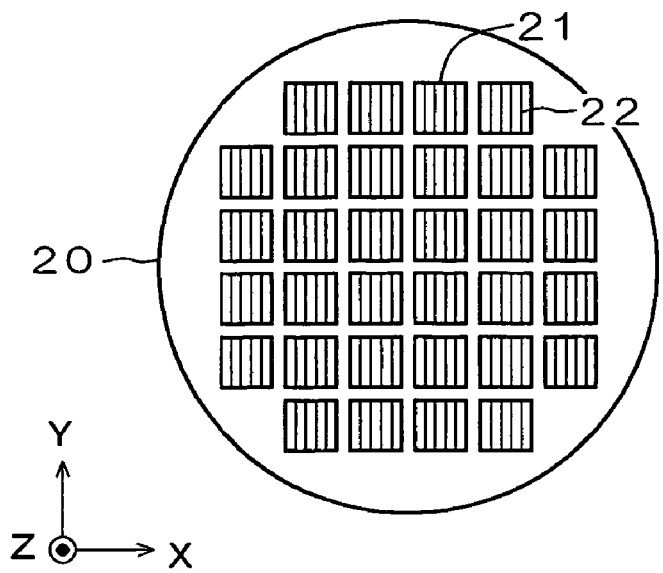
FIG. 2 shows an external view of a surface of a semiconductor wafer 20.
Figure 3:
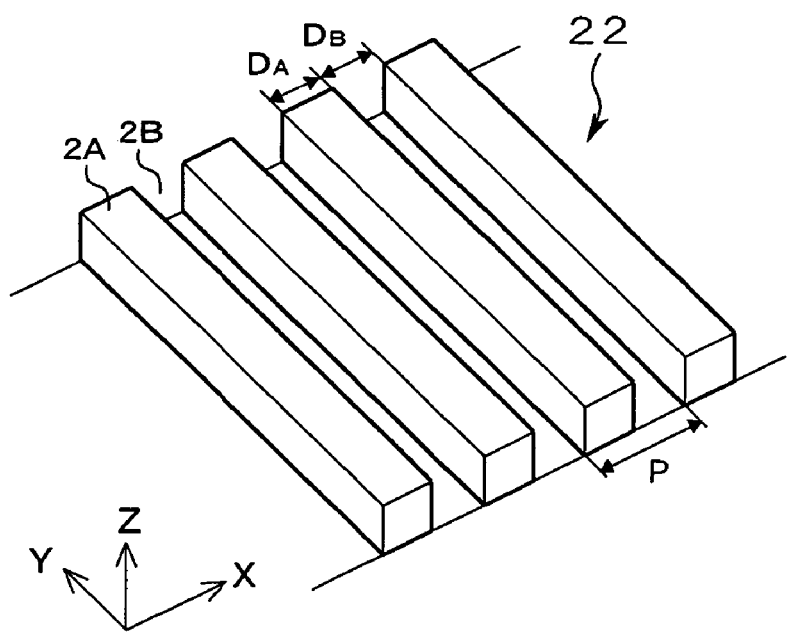
FIG. 3 is a perspective view showing a corrugation structure of a repetitive pattern 22.

As shown in FIG. 2, a plurality of chip regions 21 is arranged in the X and Y directions on the surface of the semiconductor wafer 20 and repetitive pattern 22 is formed in each chip region 21. The repetitive pattern 22 is a resist pattern (for example, an interconnection pattern) in which a plurality of line portions 2A is arranged at a constant pitch P along the width direction as shown in FIG. 3. A space between neighboring line portions 2A is a space portion 2B. The direction of arrangement of the line portion 2A (X direction) is referred to as "the repetition direction of the repetitive pattern 22".

Here, it is assumed that the designed value of a line width $D_A$ of the line portion 2A of the repetitive pattern 22 is ½ of the pitch P. When the repetitive pattern 22 is formed in accordance with the designed value, the line width $D_A$ of the line portion 2A becomes equal to a line width $D_B$ of the space portion 2B and the volume ratio between the line portion 2A and the space portion 2B is almost 1:1. In contrast to this, if the exposure focus during the process of forming the repetitive pattern 22 deviates from an proper value, the pitch P remains the same, however, the line width $D_A$ of the line portion 2A comes to differ from the designed value and therefore, also comes to differ from the line width $D_B$ of the space portion 2B, and the volume ratio between the line portion 2A and the space portion 2B deviates from almost 1:1.

The surface inspection apparatus 10 in the first embodiment performs a defect inspection of the repetitive pattern 22 by utilizing the change in the volume ratio between the line portion 2A and the space portion 2B of the above-mentioned repetitive pattern 22. For simplicity of explanation, it is assumed that an ideal volume ratio (designed value) is 1:1. The change in the volume ratio results from the deviation of the exposure focus from a proper value and appears in each shot region of the semiconductor wafer 20. Here, the volume ratio can be referred to in other words as an area ratio of a section shape.

Moreover, in the first embodiment, it is assumed that the pitch P of the repetitive pattern 22 is sufficiently small compared to the wavelength of illumination light (to be described later) for the repetitive pattern 22. Because of this, it is unlikely that diffracted light is emitted from the repetitive pattern 22, therefore, it is not possible to perform a defect inspection of the repetitive pattern 22 using the diffracted light. The principle of the defect inspection in the first embodiment is explained below in order together with the configuration of the surface inspection apparatus 10 (FIG. 1).

The stage 11 of the surface inspection apparatus 10 mounts the semiconductor wafer 20 on its upper surface and fixes and holds it by, for example, vacuum adsorption. Further, the stage 11 can be rotated around the normal line 1A at the center of the upper surface as an axis. By means of this rotation mechanism, it is possible to rotate the repetition direction (X direction in FIG. 2 and FIG. 3) of the repetitive pattern 22 of the semiconductor wafer 20 in the surface of the semiconductor wafer 20. Here, the upper surface of the stage 11 is a horizontal plane and the stage 11 does not have a tilt mechanism. Because of this, it is possible to keep the semiconductor wafer 20 in a horizontal state at all times.

When the stage 11 is rotating, the alignment system 12 illuminates the outer edge portion of the semiconductor waver 20, detects the position in the rotation direction of an outline reference (for example, a notch) provided on the outer edge portion, and stops the stage 11 at a predetermined position. As a result, it is possible to set the repetition direction of the repetitive pattern 22 (X direction in FIG. 2 and FIG. 3) of the semiconductor wafer 20 at an inclined angle of 45 degrees with respect to an incident plane 3A of illumination light to be described later (refer to FIG. 4).

The illumination system 13 is an eccentric optical system including a light source 31, a wavelength selection filter 32, a light guide fiber 33, a polarization filter 34, and a concave reflection mirror 35, and the repetitive pattern 22 of the semiconductor wafer 20 on the stage 11 is illuminated with linearly polarized light L1. The linearly polarized light L1 is an illumination light for the repetitive pattern 22. The entire surface of the semiconductor wafer 20 is irradiated with the linearly polarized light L1.

Figure 4:
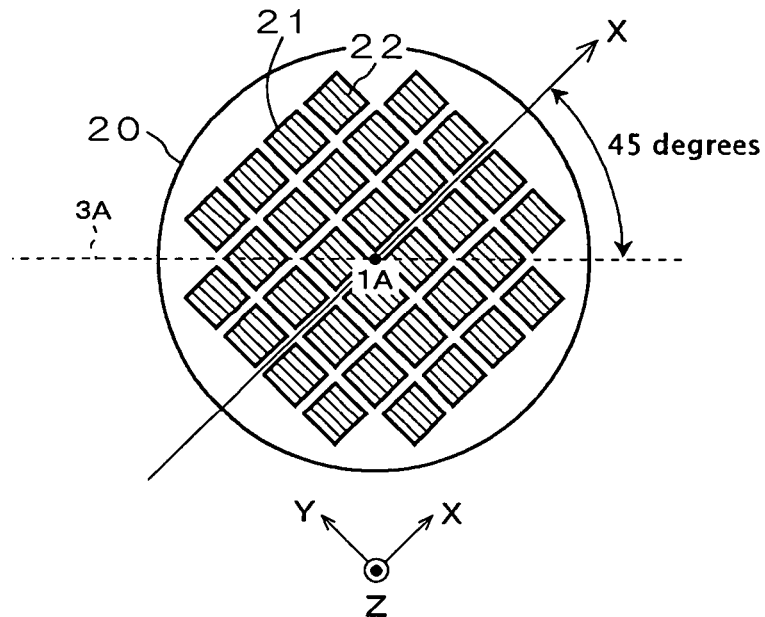
FIG. 4 is a diagram showing an inclined state of an incidence plane (3A) of linearly polarized light L1 and the repetition direction (X direction) of the repetitive pattern 22.

The propagating direction of the linearly polarized light L1 (direction of the main ray of the linearly polarized light L1 that reaches an arbitrary point on the surface of the semiconductor wafer 20) is almost parallel to an optical axis O1 of the concave reflection mirror 35. The optical axis O1 passes through the center of the stage 11 and is inclined at predetermined angles θ with respect to the normal line 1A of the stage 11. Incidentally, the plane including the propagating direction of the linearly polarized light L1 and parallel to the normal line 1A of the stage 11 is the incident plane of the linearly polarized light L1. The incident plane 3A in FIG. 4 is an incident plane at the center of the semiconductor wafer 20.

Figure 5:
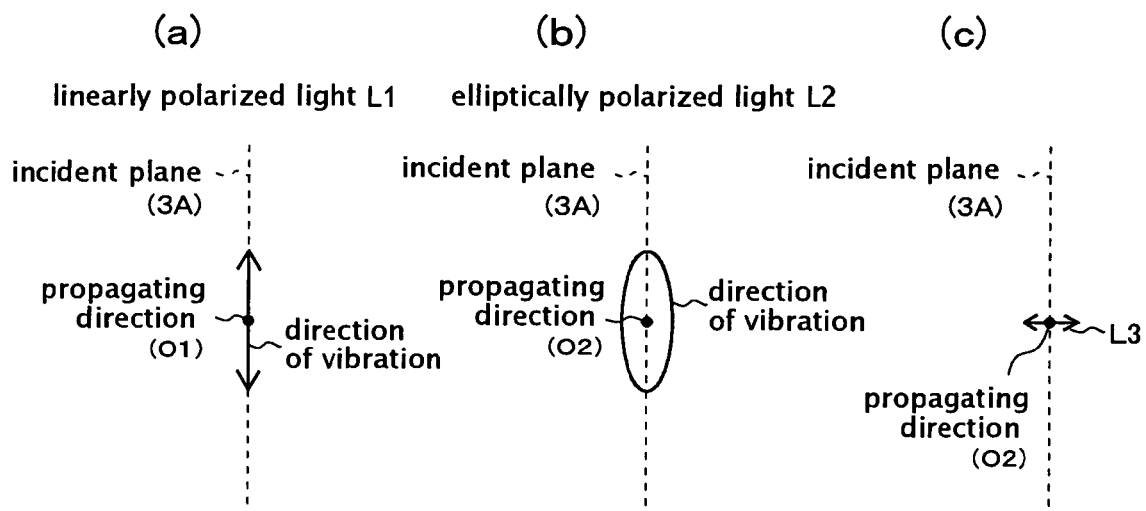
FIGS. 5(a) to 5(c) are diagrams showing the direction of vibration of the linearly polarized light L1 and elliptically polarized light L2.

Moreover, in the first embodiment, the linearly polarized light L1 is the p polarized light. In other words, as shown in FIG. 5(a), the plane including the propagating direction of the linearly polarized light L1 and the direction of the vibration of the electric (or magnetic) vector (the plane of vibration of the linearly polarized light L1) is included in the incident plane (3A) of the linearly polarized light L1. The plane of vibration of the linearly polarized light L1 is defined by the transmission axis of the polarization filter 34 arranged on the front stage of the concave reflection mirror 35.

By the way, the light source 31 of the illumination system 13 is an inexpensive discharge light source such as a metal halide lamp and a mercury lamp. The wavelength selection filter 32 allows a bright line spectrum having a predetermined wavelength among light from the light source 31 to pass through selectively. The light guide fiber 33 transmits light from the wavelength selection filter 32. The polarization filter 34 is arranged in the vicinity of the outgoing end of the light guide fiber 33 and its transmission axis is set to a predetermined orientation, making light from the light guide fiber 33 linearly polarized in accordance with this transmission axis. The concave reflection mirror 35 is a reflection mirror whose reflection surface is an inner surface of a sphere and arranged so that its front focus almost coincides with the outgoing end of the light guide fiber 33 and its rear focus positions almost coincides with the surface of the semiconductor wafer 20, and guides a light from the polarization filter 34 to the surface of the semiconductor wafer 20. The illumination system 13 is a telecentric optical system for the semiconductor wafer 20 side.

In the above-mentioned illumination system 13, the light from the light source 31 passes through the wavelength selection filter 32, the light guide fiber 33, the polarization filter 34, and the concave reflection mirror 35, turns into the linearly polarized light L1 with the p polarization (FIG. 5(a)) and is incident on the entire surface of the semiconductor wafer 20. The respective incidence angles of the linearly polarized light L1 at respective points of the semiconductor wafer 20 are equal to each other, corresponding to an angle θ formed by the optical axis O1 and the normal line 1A.

In the first embodiment, since the linearly polarized light L1 incident on the semiconductor wafer 20 is the p polarized light (FIG. 5(a)), when the repetition direction (X direction) of the repetitive pattern 22 of the semiconductor wafer 20 is set to 45 degrees with respect to the incident plane (3A) of the linearly polarized light L1 as shown in FIG. 4, the angle between the direction (V direction in FIG. 6) of the intersecting line of the plane of vibration and of the surface of the semiconductor wafer 20 and the repetition direction (X direction) of the repetitive pattern 22 is also set to 45 degrees.

In other words, the linearly polarized light L1 enters the repetitive pattern 22 in such a manner as to obliquely transverse the repetitive pattern 22 in a state in which the direction (V direction in FIG. 6) of the intersecting line of the plane of vibration and of the surface of the semiconductor wafer 20 is inclined at 45 degrees with respect to the repetition direction (X direction) of the repetitive pattern 22.

Such a state of the angle between the linearly polarized light L1 and the repetitive pattern 22 is uniform on the entire surface of the semiconductor wafer 20. Here, even if 45 degrees are replaced with any one of 135 degrees, 225 degrees, and 315 degrees, the state of the angle between the linearly polarized light L1 and the repetitive pattern 22 remains the same. Further, the angle formed by the direction of the plane of vibration in FIG. 6 (V direction) and the repetition direction (X direction) is set to 45 degrees because the sensitivity of the defect inspection of the repetitive pattern 22 is made maximum.

Then, when the repetitive pattern 22 is illuminated with the above-mentioned linearly polarized light L1, elliptically polarized light L2 is emitted from the repetitive pattern 22 in the specular direction (FIG. 1, FIG. 5(b)). In this case, the propagating direction of the elliptically polarized light L2 coincides with the specular direction. The specular direction is a direction included in the incident plane (3A) of the linearly polarized light L1 and inclined at the angle θ with respect to the normal 1A of the stage 11 (an angle equal to the incidence angle θ of the linearly polarized light L1). Here, since the pitch P of the repetitive pattern 22 is sufficiently small compared to the illumination wavelength, it is unlikely that diffracted light is emitted from the repetitive pattern 22.

Here, the reason why the linearly polarized light L1 turns into an elliptic polarization by the repetitive pattern 22 and the elliptically polarized light L2 is emitted from the repetitive pattern 22 is explained briefly. When the linearly polarized light L1 is incident on the repetitive pattern 22, the direction of the plane of vibration (V direction in FIG. 6) is divided into two polarized light components $V_X$ and $V_Y$ shown in FIG. 7. The polarized light component $V_X$, on one hand, is a component parallel to the repetition direction (X repetition). The polarized light component $V_Y$, on the other hand, is a component perpendicular to the repetition direction (X direction). Then, the two polarized light components $V_X$ and $V_Y$ are subjected to the different amplitude changes and phase changes independently of each other. The amplitude change and the phase change are different because the complex reflectivity (that is, the amplitude reflectivity of a complex number) is different resulting from the anisotropy of the repetitive pattern 22 and is referred to as the form birefringence. As a result, the reflected lights of the two polarized light components $V_X$ and $V_Y$ differ in amplitude and phase from each other and the reflected light, which is a combination of the components, becomes the elliptically polarized light L2 (FIG. 5(b)).

Further, it is assumed that the degree of ellipseness due to the anisotropy of the repetitive pattern 22 is equal to a polarized light component L3 (FIG. 5(c)) perpendicular to the plane of vibration (identical to the incident plane (3A) in the first embodiment) of the linearly polarized light L1 in FIG. 5(a) among the elliptically polarized light L2 in FIG. 5(b). Then, the magnitude of the polarized light component L3 depends on the material and the shape of the repetitive pattern 22 and the angle between the direction of the plane of vibration (V direction) in FIG. 6 and the repetition direction (X direction). Because of this, to keep the angle between the V direction and the X direction to a constant value (45 degrees in the first embodiment), as the shape of the repetitive pattern 22 changes, the degree of ellipseness (the magnitude of the polarized light component L3) changes accordingly even when the material of the repetitive pattern 22 is constant.

Figure 8:
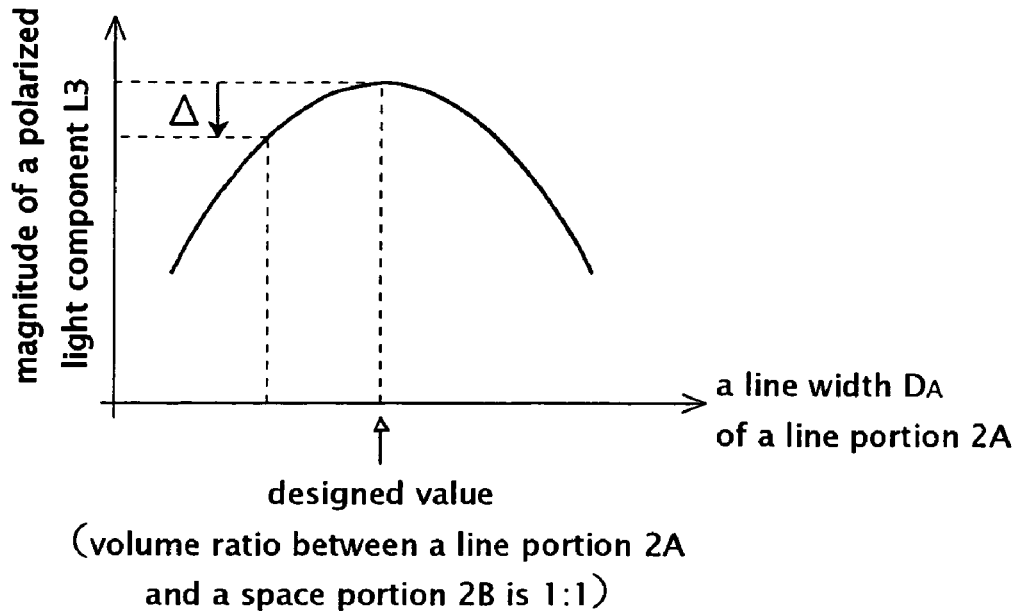
FIG. 8 is a diagram showing a relationship between the magnitude of a polarized light component L3 and a line width $D_A$ of a line portion 2A of the repetitive pattern 22.

The relationship between the shape of the repetitive pattern 22 and the magnitude of the polarized light component L3 is described below. As shown in FIG. 3, the repetitive patterns 22 have a corrugation shape, in which the line portions 2A and the space portions 2B are arranged alternately along the X direction and if they are formed in accordance with the designed values with a proper exposure focus, the line width $D_A$ of the line portion 2A is equal to the line width $D_B$ of the space portion 2B and the volume ratio between the line portion 2A and the space portion 2B is almost 1:1. In such a case of the ideal shape, the magnitude of the polarized light component L3 becomes maximum. In contrast to this, if the exposure focus deviates from the proper value, the line width $D_A$ of the line portion 2A and the line width $D_B$ of the space portion 2B become different and the volume ratio between the line portion 2A and the space portion 2B deviates from almost 1:1. In this case, the magnitude of the polarized light component L3 becomes smaller compared to that in the ideal case. The change in the magnitude of the polarized light component L3 is schematically shown in FIG. 8. The horizontal axis in FIG. 8 represents the line width $D_A$ of the line portion 2A.

Figure 6:
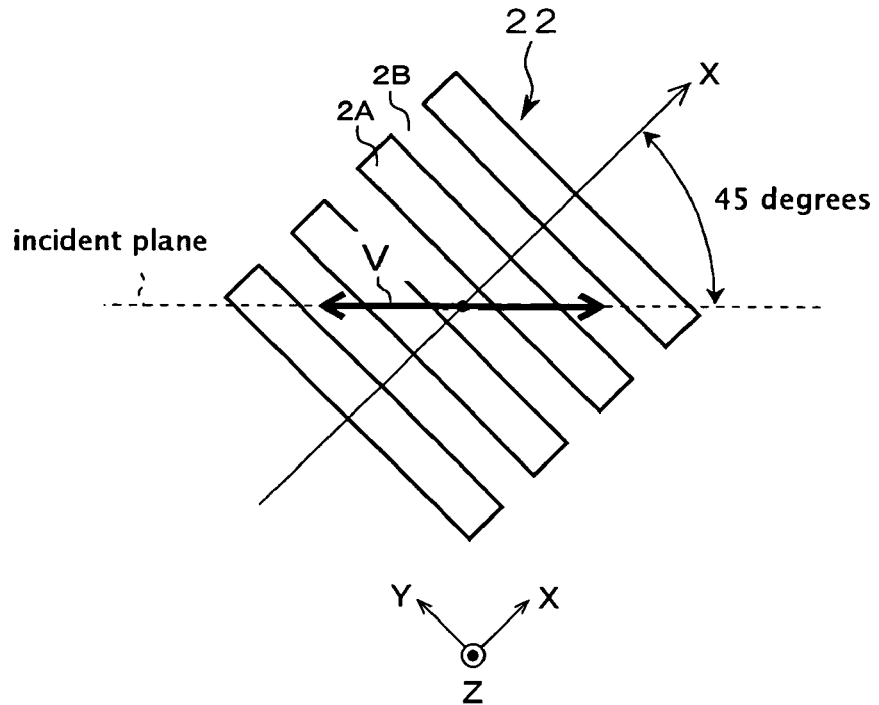
FIG. 6 is a diagram showing an inclined state of the direction of vibration plane (V direction) of the linearly polarized light L1 and the repetition direction (X direction) of the repetitive pattern 22.
Figure 7:
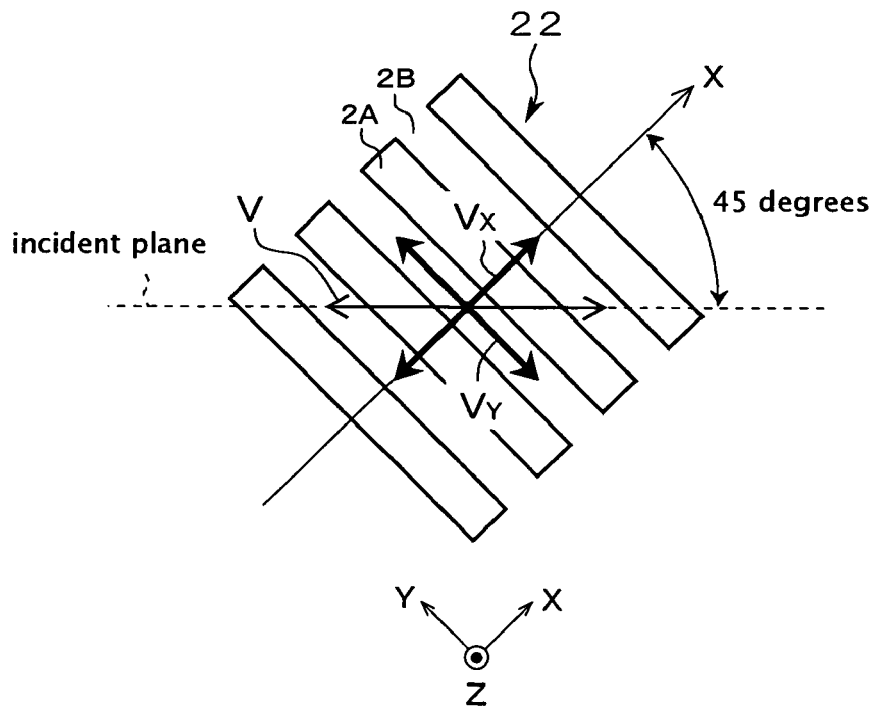
FIG. 7 is a diagram showing how light is divided into a polarized light component $V_X$ parallel to the repetition direction (X direction) and a polarized light component $V_Y$ perpendicular thereto.

As described above, if the repetitive pattern 22 is illuminated using the linearly polarized light L1 in a state in which the direction (V direction) of the plane of vibration in FIG. 6 is inclined at 45 degrees with respect to the repetition direction (X direction) of the repetitive pattern 22, the degree of ellipseness (the magnitude of the polarized light component L3 in FIG. 5(c)) of the elliptically polarized light L2 (FIG. 1, FIG. 5(b)) that has been emitted in the specular direction depends on the shape of the repetitive pattern 22 (the volume ratio between the line portion 2A and the space portion 2B) (FIG. 8). The propagating direction of the elliptically polarized light L2 is included in the incident plane (3A) of the linearly polarized light L1 and inclined at the angle θ (an angle equal to the incidence angle θ of the linearly polarized light L1) with respect to the normal line 1A of the stage 11.

Next, the light detecting system 14 is described. As shown in FIG. 1, the light detecting system 14 is an eccentric optical system including a concave reflection mirror 36, an image formation lens 37, a polarization filter 38, and an image pickup device 39.

The concave reflection mirror 36 is the same reflection mirror as the concave reflection mirror 35 in the above-mentioned illumination system 13, with its optical axis O2 passing through the center of the stage 11 and is arranged so as to be inclined at the angle θ with respect to the normal line 1A of the stage 11. Therefore, the elliptically polarized light L2 from the repetitive pattern 22 propagates along the optical axis O2 of the concave reflection mirror 36 as a result. The concave reflection mirror 36 reflects the elliptically polarized light L2 and guides it toward the image formation lens 37 and condenses it on the image pickup plane of the image pickup device 39 in cooperation with the image formation lens 37.

However, between the image formation lens 37 and the concave reflection mirror 36, the polarization filter 38 is arranged. The orientation of the transmission axis of the polarization filter 38 is set so as to be perpendicular to the transmission axis of the polarization filter 34 in the above-mentioned illumination system 13 (the cross Nicol state). Therefore, it is possible for the polarization filter 38 to extract only a polarized light component L4 (FIG. 1) corresponding to the polarized light component L3 in FIG. 5(c) of the elliptically polarized light L2 and guide it to the image pickup device 39. As a result, on the image pickup plane of the image pickup device 39, the reflected image of the semiconductor wafer 20 by the polarized light component L4 is formed.

The image pickup device 39 is, for example, a CCD image pickup device, and opto-electrically converts the reflected image of the semiconductor wafer 20 formed on the image pickup plane and outputs an image signal to the image processing device 15. The contrast of the reflected image of the semiconductor wafer 20 is almost in proportion to the light intensity of the polarized light component L4 (the magnitude of the polarized light component L3 in FIG. 5(c)) and changes in accordance with the shape of the repetitive pattern 22 (the volume ratio between the line portion 2A and the space portion 2B) (refer to FIG. 8). The reflected image of the semiconductor wafer 20 is brightest when the repetitive pattern 22 have the ideal shape (the volume ratio is 1:1). Here, the contrast of the reflected image of the semiconductor wafer 20 appears in each shot region.

The image processing device 15 captures the reflected image of the semiconductor wafer 20 based on the image signal output from the image pickup device 39. Incidentally, the image processing device 15 stores the reflected image of the conforming wafer in advance for comparison. The conforming wafer has the repetitive pattern 22 of ideal shape (the volume ratio is 1:1) formed on the entire surface. The brightness information of the reflected image of the conforming wafer shows the highest brightness value.

Therefore, after capturing the reflected image of the semiconductor wafer 20, which is a substrate to be inspected, the image processing device 15 compares its brightness information with the brightness information of the reflected image of the conforming wafer. Then, based on the amount of drop in the brightness value at a dark portion of the reflected image of the semiconductor wafer 20 (∝ the amount of drop Δ in FIG. 8), the image processing device 15 detects defects of the repetitive pattern 22 (the change in the volume ratio between the line portion 2A and the space portion 2B). For example, it is only necessary to judge that it is "defective" when the amount of drop in the brightness value is larger than a predetermined threshold value (allowable value) and "normal" when it is smaller than the threshold value.

By the way, in addition to the configuration in which the reflected image of the conforming wafer is stored in advance as described above, the image processing device 15 may have a configuration in which arrangement data and the threshold value of the brightness value in the shot region of the wafer are stored in advance.

In this case, the position of each shot region in the captured reflected image of the wafer is known based on the arrangement data of the shot region, the brightness value in each shot region is found. Then, by comparing the brightness value and the stored threshold value, defects of the patterns are detected. It is only necessary to judge a shot region the brightness value of which is smaller than the threshold value as a defect.

As described above, according to the surface inspection apparatus 10 in the first embodiment, the repetitive pattern 22 is illuminated using the linearly polarized light L1 in a state in which the direction of the plane of vibration (V direction) in FIG. 6 is inclined with respect to the repetition direction (X direction) of the repetitive pattern 22 and at the same time, defects of the repetitive pattern 22 are detected based on the light intensity of the polarized light component L4 (the magnitude of the polarized light component L3 in FIG. 5(c)) among the elliptically polarized light L2 that has been emitted in the specular direction, therefore, even if the pitch P of the repetitive pattern 22 is sufficiently small compared to the illumination wavelength, it is possible to securely perform a defect inspection. In other words, it is possible to securely cope with reduction of the repetition pitch without the need to shorten the wavelength of the linearly polarized light L1, which is the illumination light.

Further, in the surface inspection apparatus 10 in the first embodiment, the angle formed by the direction (V direction) of the plane of vibration in FIG. 6 and the repetition direction (X direction) is set to 45 degrees, therefore, it is possible to extract the amount of drop in the brightness value ($\propto$ the amount of drop $\Delta$ in FIG. 8) of the reflected image of the semiconductor wafer 20 with good sensitivity, therefore, it is possible to perform a highly sensitive defect inspection of the repetitive pattern 22.

Moreover, in the surface inspection apparatus 10 in the first embodiment, performing the defect inspection of the repetitive pattern 22 is not limited to the case where the pitch P of the repetitive pattern 22 is sufficiently small compared to the wavelength of the illumination light, but it is also possible when the pitch P of the repetitive pattern 22 is about the same as the wavelength of the illumination light and even when it is greater than the wavelength of the illumination light. In other words, regardless of the pitch P of the repetitive pattern 22, it is possible to perform the defect inspection without fail. This is because the turning into an elliptic polarization of the linearly polarized light L1 due to the repetitive pattern 22 results from the volume ratio between the line portion 2A and the space portion 2B of the repetitive pattern 22 but does not depend on the pitch P of the repetitive pattern 22.

Further, in the surface inspection apparatus 10 in the first embodiment, if the volume ratio between the line portion 2A and the space portion 2B of the repetitive pattern 22 is the same, the amount of drop in the brightness value ($\propto$ the amount of drop $\Delta$ in FIG. 8) of the reflected image becomes the same. Because of this, regardless of the pitch P of the repetitive pattern 22, the detection can be performed with the same sensitivity as long as the amount of change in the volume ratio is the same. For example, as the repetitive pattern 22 shown in FIG. 9(a) and FIG. 9(b), when the pitch P is different and the volume ratio between the line portion 2A and the space portion 2B is the same, it is possible to perform a defect inspection with the same sensitivity. As can be seen from the comparison in FIG. 9(a) and FIG. 9(b), the smaller the pitch P is; the smaller change in shape (the amount of deviation $\delta$ of the line width $D_A$ of the line portion 2A from the designed value) can be detected securely.

In the surface inspection apparatus 10 in the first embodiment, even when the pitch P of the repetitive pattern 22 is different, it is possible to perform inspection while maintaining the semiconductor wafer 20 in a horizontal state (without performing the conventional tilt adjustment of the stage), it is possible to securely reduce the preparation time before a defect inspection actually begins (that is, the time until the reflected image of the semiconductor wafer 20 is captured) and therefore improve the operation efficiency.

Further, in the surface inspection apparatus 10 in the first embodiment, the stage 11 does not have the tilt mechanism, therefore, the device configuration can be simplified. In addition, an inexpensive discharge light source can be used as the light source 31 of the illumination system 13, therefore, the total configuration of the surface inspection apparatus 10 becomes inexpensive and simple.

Figure 10:
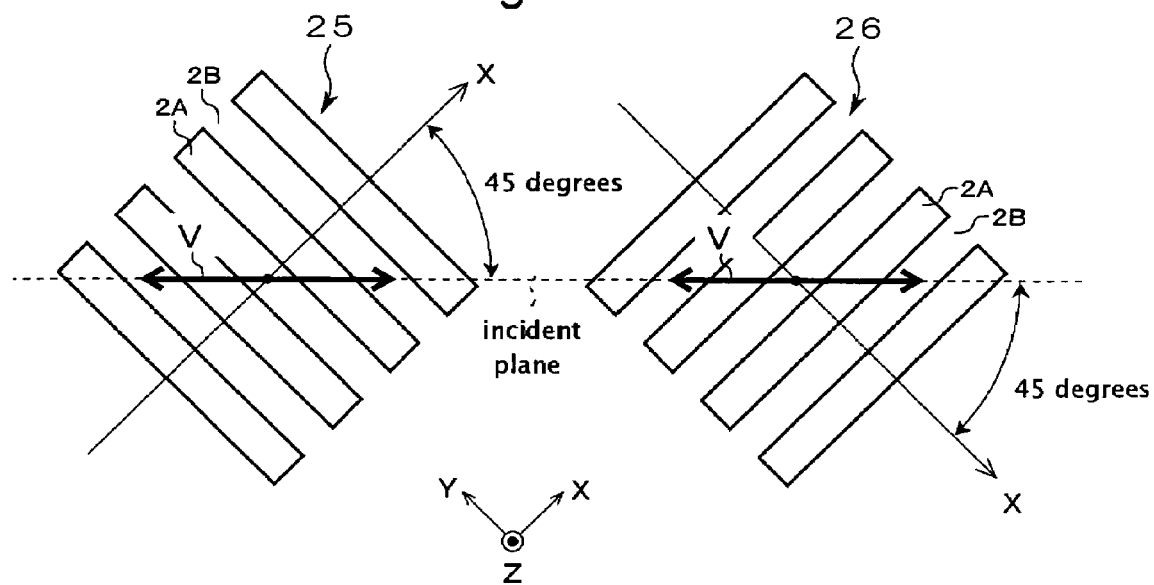
FIG. 10 is a diagram showing repetitive patterns 25 and 26 whose repetition directions are different.

Moreover, for the surface inspection apparatus 10 in the first embodiment, it is possible to easily perform a defect inspection of all of the repetitive patterns, even when a plurality of kinds of repetitive patterns is formed on the surface of the semiconductor wafer 20 and the repetitive patterns different in the pitch P or the repetition direction (X direction) are present mixedly, by capturing the reflected image of the entire surface of the semiconductor wafer 20 and investigating the amount of drop in the brightness value at each portion. Note that, as shown in FIG. 10, the repetitive patterns different in the repetition direction are repetitive patterns 25 in the zero-degree direction and repetitive patterns 26 in the 90-degree direction. These repetitive patterns 25 and 26 differ 90 degrees from each other in the repetition direction (X direction). However, the angle formed by the repetition direction (X direction) and the direction of the plane of vibration (V direction) of the linearly polarized light L1 is 45 degrees, respectively.

Furthermore, for the surface inspection apparatus 10 in the first embodiment, it is also possible to obtain defect information relating to the asymmetry of the edge shape of the line portion 2A of the repetitive pattern 22 (for example, the directivity of collapse of the edge shape) because the linearly polarized light L1 is made incident obliquely with respect to the surface of the semiconductor wafer 20 (refer to FIG. 1). To this end, it becomes necessary to rotate by 180 degrees the repetition direction (X direction) of the repetitive pattern 22 of the semiconductor wafer 20 by the stage 11, capture the reflected image of the semiconductor wafer 20 in the states before and after the rotation, and investigate the difference in the brightness at the same portion.

Figure 11:
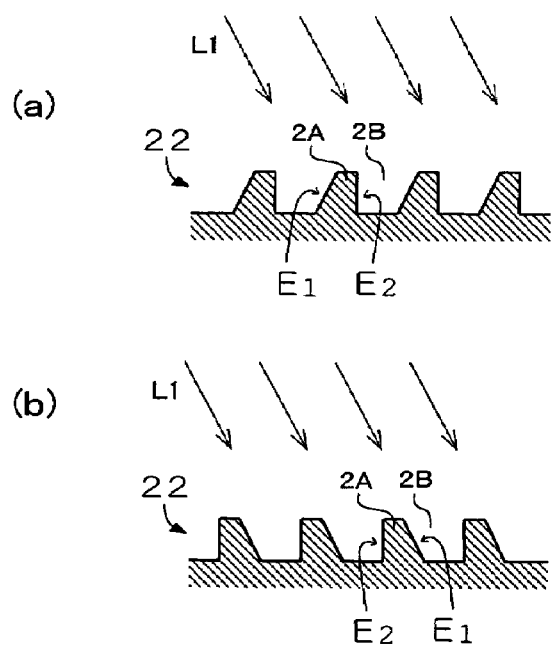
FIGS. 11(a) and 11(b) are diagrams showing a relationship between the repetitive pattern 22 with asymmetric edge shape and the incidence direction of the linearly polarized light L1.

FIG. 11 schematically shows the relationship between the repetitive pattern 22 the edge shape of which is asymmetric and the incidence direction of the linearly polarized light L1. For example, FIG. 11(a) shows a state before the 180-degree rotation and the illumination light is made incident through the edge ($E_1$) side that has collapsed between the edges $E_1$ and $E_2$ of the line portion 2A. FIG. 11(b) shows a state after the 180-degree rotation and the illumination light is made to enter through the edge ($E_2$) side that has not collapsed between the two edges $E_1$ and $E_2$. Then, the brightness value of the reflected image captured in each state reflects the edge shape of the edges $E_1$ and $E_2$ in the incidence direction and in this example, the brightness value of the reflected image is larger in the case shown in FIG. 11(a). Therefore, by investigating the difference in the brightness of the reflected image before and after rotated by 180 degrees, the asymmetry of the edge shape of the line portion 2A is known. It may also be possible to perform a defect inspection by combining the reflected images before and after 180-degree rotation.

Note that as in the first embodiment, when the linearly polarized light L1 is made incident obliquely with respect to the surface of the semiconductor waver 20 (refer to FIG. 1, the incidence angle θ), to be strict, the elliptically polarized light L2 (FIG. 5(b)) that is emitted from the repetitive pattern 22 rotates slightly with its propagating direction as an axis. Because of this, it is preferable to fine-adjust the orientation of the transmission axis of the polarization filter 38 in the light detecting system 14 taking this rotation angle into consideration. In the state after fine adjustment, the orientation of the transmission axis of the polarization filters 34 and 38 is no longer 90 degrees accurately, however, such an angle also belongs to the category of "perpendicular (or orthogonal)" and the state can be said as the cross Nicol state. It is possible to improve the inspection precision by fine-adjusting the orientation of the transmission axis of the polarization filter 38. As one example of the fine adjustment method is to capture an image by reflecting the linearly polarized light L1 on the surface without repetitive patterns and to rotate the orientation of the transmission axis of the polarization filter 38 so that the brightness value of the image is to be minimum.

Moreover, in the above-mentioned first embodiment, an example in which the linearly polarized light L1 is the p polarized light is described, however, the present invention is not limited to this. Instead of the p polarized light, an s polarized light may be used. The s polarized light is linearly polarized light whose plane of vibration is perpendicular to the incident plane. Because of this, as shown in FIG. 4, when the repetition direction (X direction) of the repetitive pattern 22 of the semiconductor wafer 20 is set to an angle of 45 degrees with respect to the incident plane (3A) of the s polarized light, which is the linearly polarized light L1, the angle between the direction of the intersecting line of the plane of vibration of the s polarized light and of the surface of the semiconductor wafer 20 and the repetition direction (X direction) of the repetitive pattern 22 is also set to 45 degrees. Incidentally, the p polarized light has an advantage in acquiring defect information relating to the edge shape of the line portion 2A of the repetitive pattern 22. The s polarized light efficiently extracts defect information about the surface of the semiconductor waver 20 and is advantageous in improving the SN ratio.

Furthermore, not limited to the p polarized light or s polarized light, but linearly polarized light whose plane of vibration has an arbitrary inclination with respect to the incident plane may be accepted. In this case, it is preferable to set the repetition direction (X direction) of the repetitive pattern 22 to an angle other than 45 degrees with respect to the incident plane of the linearly polarized light L1 and set the angle between the direction of the intersecting line of the plane of vibration of the linearly polarized light L1 and of the surface of the semiconductor wafer 20 and the repetition direction (X direction) of the repetitive pattern 22 to 45 degrees.

Second Embodiment

Here, a surface inspection apparatus 40 including an illumination system (41 to 46) and a light detecting system (45 to 49) shown in FIG. 12(a) instead of the illumination system 13 and the light detecting system 14 of the surface inspection apparatus 10 (FIG. 1) in the first embodiment is described. In FIG. 12(a), the stage 11, the alignment system 12, and the image processing device 15 similar to those in the first embodiment are not shown schematically. The surface inspection apparatus 40 is also an apparatus that automatically performs inspection of the surface of the semiconductor wafer 20 in the production process of a semiconductor circuit device.

The illumination system (41 to 46) and the light detecting system (45 to 49) of the surface inspection apparatus 40 in the second embodiment are described. The illumination system (41 to 46) includes a light source 41, a wavelength selection filter 42, a relay lens 43, an aperture diaphragm 44, a polarized light beam splitter 45, and a lens 46. Among these, the polarized light beam splitter 45 and the lens 46 function also as a part of the light detecting system (45 to 49). The light detecting system (45 to 49) includes an aperture diaphragm 47, an image formation lens 48, and an image pickup device 49, in addition to the polarized light beam splitter 45 and the lens 46. An optical axis O3 of the lens 46 coincides with the normal line 1A of the stage 11 (refer to FIG. 1).

The surface inspection apparatus 40 is one provided with the lens 46 instead of the concave reflection mirrors 35 and 36 of the surface inspection apparatus 10 in FIG. 1, which has both the functions thereof, and with the polarized light beam splitter 45 instead of the polarization filters 34 and 38 of the surface inspection apparatus 10, which has both the functions thereof. As described above, the optical elements (45, 46) of the illumination system (41 to 46) and the light detecting system (45 to 49) are made common, therefore, the number of parts can be reduced and the configuration can be simplified.

Here, the light source 41, the wavelength selection filter 42, the image formation lens 48, and the image pickup device 49 are the same as the above-mentioned light source 31, the wavelength selection filter 32, the image formation lens 37, and the image pickup device 39. The aperture diaphragms 44 and 47 are arranged in the vicinity of the focus of the lens 46. The aperture diaphragm 47 is an optical element for shielding stray light. The polarized light beam splitter 45 reflects only linearly polarized light whose plane of vibration is perpendicular to the surface of the paper and allows only linearly polarized light whose plane of vibration is parallel to the surface of the paper to pass through. In other words, the reflection axis and the transmission axis of the polarized light beam splitter 45 are perpendicular to each other with respect to the orientation (the cross Nicol state).

In the illumination system (41 to 46), light from the light source 41 enters the polarized light beam splitter 45 via the wavelength selection filter 42, the relay lens 43, and the aperture diaphragm 44 and the light reflected therefrom (that is, the linearly polarized light L1 whose plane of vibration is perpendicular to the surface of the paper) is guided to the lens 46. Then, after passing through the lens 46, the linearly polarized light L1 from the polarized light beam splitter 45 incidents perpendicularly on the entire surface of the semiconductor wafer 20. In the case of perpendicular incidence, the incident plane of the linearly polarized light L1 cannot be defined. The direction of an intersecting line of a plane of vibration of the linearly polarized light L1 and of the surface of the semiconductor waver 20 is shown as "V direction" in FIG. 12(b).

The semiconductor wafer 20 is set so that the repetition direction (X direction) of the repetitive pattern 22 is inclined at 45 degrees with respect to the direction of the plane of vibration of the linearly polarized light L1 (V direction) by the stage 11 and the alignment system 12 as those in FIG. 1. The angle formed by the V direction and the X direction is set to 45 degrees in an attempt to maximize the sensitivity of the defect inspection of the repetitive pattern 22. Such a state of the angle between the linearly polarized light L1 and the repetitive pattern 22 is uniform on the entire surface of the semiconductor wafer 20.

Then, when the repetitive pattern 22 is illuminated with the above-mentioned linearly polarized light L1, an elliptically polarized light L2 is emitted from the repetitive pattern 22 of the semiconductor wafer 20 in the specular direction (in the direction of the optical axis O3). The reason for turning into an elliptic polarization is the same as that in the first embodiment and in the case of perpendicular incidence, the phase change is the same between the polarized light component $V_X$ parallel to the repetition direction (X direction) and the polarized light component $V_Y$ (FIG. 7) perpendicular thereto. In other words, the polarized light components $V_X$ and $V_Y$ are subjected to different amplitude changes independently of each other. Because of this, the reflected light of the polarized light components $V_X$ and $V_Y$ differ in amplitude and the reflected light, which is a combination of these components, becomes the elliptically polarized light L2. Incidentally, the form birefringence in the case of perpendicular incidence corresponds to the fact that the amplitude reflectivity differs resulting from the anisotropy of the repetitive pattern 22.

The elliptically polarized light L2 from the repetitive pattern 22 is condensed again by the lens 46 and after passing through the polarized light beam splitter 45, the aperture diaphragm 47, and the image formation lens 48, it is condensed on the image pickup plane of the image pickup device 49. The polarized light beam splitter 45 extracts only the polarized light component L4 perpendicular to the plane of vibration (parallel to the surface of the paper) of the linearly polarized light L1 among the elliptically polarized light L2 and guides it to the image pickup device 49. On the image pickup plane of the image pickup device 49, a reflected image of the semiconductor wafer 20 by the polarized light component L4 is formed. The contrast of the reflected image is almost proportional to the light intensity of the polarized light component L4.

The light intensity of the polarized light component L4 changes in accordance with the shape of the repetitive pattern 22 (the volume ratio between the line portion 2A and the space portion 2B) (refer to FIG. 8). However, it is assumed that angle between the direction of the plane of vibration of the linearly polarized light L1 (V direction) and the repetition direction (X direction) is kept to a constant value (45 degrees in the second embodiment) and the material property of the repetitive pattern 22 is constant. The light intensity of the polarized light component L4 is maximum when the shape of the repetitive pattern 22 is ideal (the volume ratio is 1:1).

Here, the form birefringence (the difference in the amplitude reflectivity resulting from the anisotropy of the repetitive pattern 22) in the case of perpendicular incidence is described and the relationship between the shape of the repetitive pattern 22 and the light intensity of the polarized light component L4 is described. For this description, the repetitive pattern 22 is modeled. In other words, it is assumed that a plurality of layers composed of a substance 1 with thickness $t_1$ and dielectric constant $\in_1$ and a substance 2 with thickness $t_2$ and dielectric constant $\in_2$ are arranged on a plane with a sufficiently short repetition period compared to the illumination wavelength.

Figure 13:
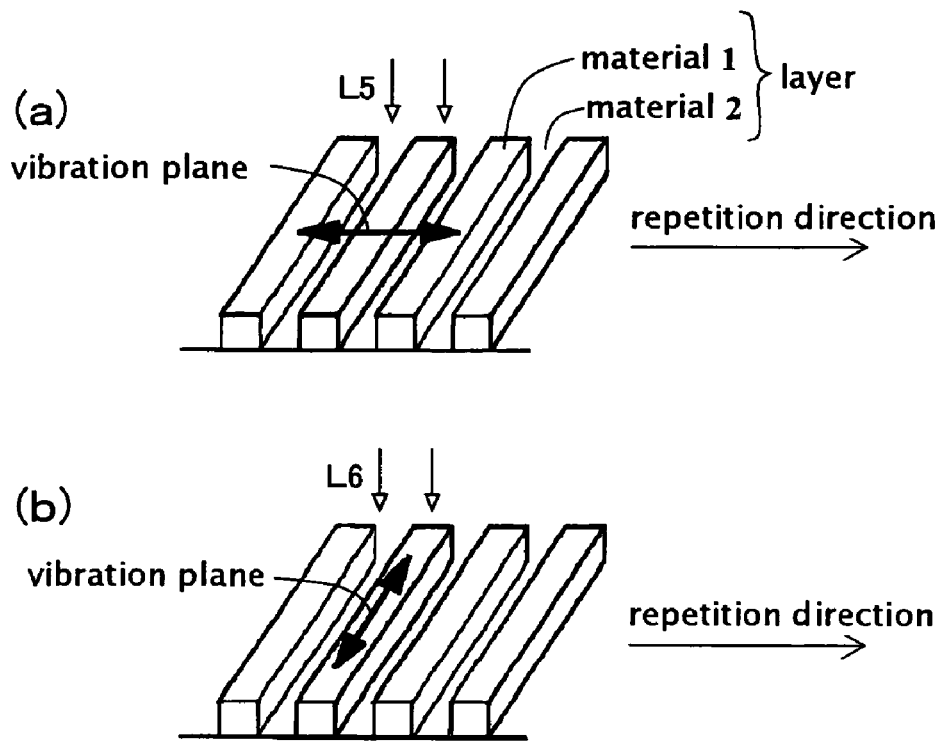
FIGS. 13(a) and 13(b) are diagrams showing the plane of vibration of a linearly polarized light L5 and L6, respectively, and the repetition direction of layers in the form birefringence for a perpendicular incidence.

As shown in FIG. 13(a), when the layer is irradiated with linearly polarized light L5 whose plane of vibration is parallel to the repetition direction of the layer, an electric field is applied so as to traverse the layer, and then small polarization occurs in accordance with the electric field. In other words, each layer generates polarization in series for the electric field. The apparent dielectric constant $\in_X$ in this case can be expressed by the following expression (1). Then, in the case of perpendicular incidence, the amplitude reflectivity $r_X$ in the substance with dielectric constant $\in_X$ can be expressed by the following expression (2).

$$\varepsilon_X = \frac{(t_1 + t_2)\varepsilon_1\varepsilon_2}{t_1\varepsilon_2 + t_2\varepsilon_1} \quad (1)$$

$$r_X = \frac{\sqrt{\varepsilon_X} - 1}{\sqrt{\varepsilon_X} + 1} = \frac{\sqrt{(t_1 + t_2)\varepsilon_1\varepsilon_2} - \sqrt{t_1\varepsilon_2 + t_2\varepsilon_1}}{\sqrt{(t_1 + t_2)\varepsilon_1\varepsilon_2} + \sqrt{t_1\varepsilon_2 + t_2\varepsilon_1}} \quad (2)$$

As shown in FIG. 13(b), when the layer is irradiated with linearly polarized light L6 whose plane of vibration is perpendicular to the repetition direction of the layer, an electric field is applied along the lengthwise direction of the layer, and then polarization occurs in accordance with the electric field. When viewed from the electric field, the polarization in each layer is arranged in parallel. The apparent dielectric constant $\in_Y$ in this case is a weighted average of the layer thickness $(t_1+t_2)$ and can be expressed by the following expression (3). Then, in the case of perpendicular incidence, the amplitude reflectivity $r_Y$ in the substance with dielectric constant $\in_Y$ can be expressed by the following expression (4).

$$\varepsilon_Y = \frac{t_1\varepsilon_1 + t_2\varepsilon_2}{t_1 + t_2} \quad (3)$$

$$r_Y = \frac{\sqrt{\varepsilon_Y} - 1}{\sqrt{\varepsilon_Y} + 1} = \frac{\sqrt{t_1\varepsilon_1 + t_2\varepsilon_2} - \sqrt{t_1 + t_2}}{\sqrt{t_1\varepsilon_1 + t_2\varepsilon_2} + \sqrt{t_1 + t_2}} \quad (4)$$

As described above, when the directions of the plane of vibration of the linearly polarized lights L5 and L6 that enter perpendicularly (FIG. 13) are different, the apparent dielectric constants $\in_X$ and $\in_Y$ differ (expressions (1) and (3)), therefore, as a result, the amplitude reflectivities $r_X$ and $r_Y$ also differ (expressions (2) and (4)). The difference $(r_X-r_Y)$ between the amplitude reflectivities $r_X$ and $r_Y$ is considered as the form birefringence in the case of perpendicular incidence.

Figure 14:
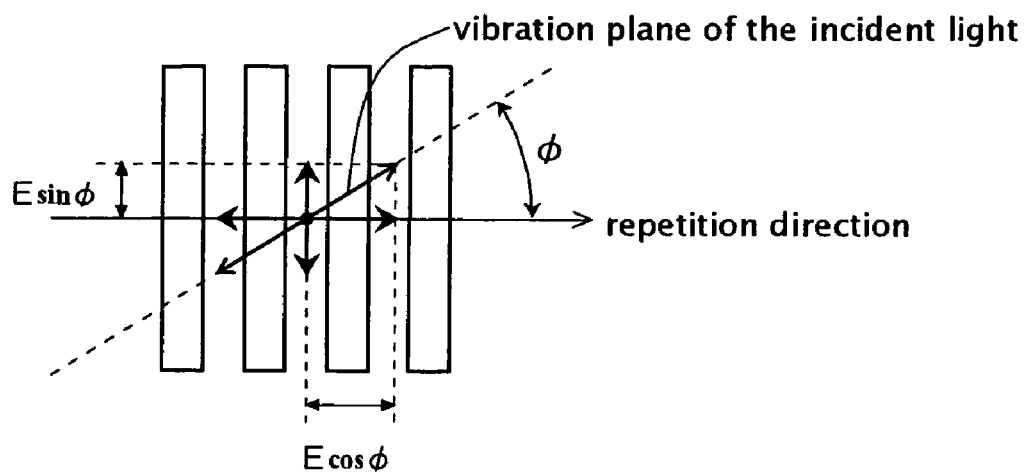
FIG. 14 is a diagram showing components parallel to and components perpendicular to the repetition direction of layers.

Next, as shown in FIG. 14, a case is considered where the plane of vibration of linearly polarized light is inclined at an angle φ with respect to the repetition direction of the layer. It is assumed that the amplitude of the linearly polarized light when it is incident on the layer is E. The linearly polarized light incident on the layer is divided into a component parallel to the repetition direction of the layer (the amplitude is E cos φ) and a component perpendicular to the repetition direction (the amplitude is E sin φ) and they are respectively subjected to the amplitude change in accordance with the above-mentioned amplitude reflectivities $r_X$ and $r_Y$ independently of each other. Because of this, the amplitude $E_X$ of the reflected light of the component parallel to the repetition direction and the amplitude $E_Y$ of the reflected light of the component perpendicular to the repetition direction are expressed by the following expressions (5) and (6). Then, the reflected light, which is a combination of the respective components whose amplitude are $E_X$ and $E_Y$, becomes the elliptically polarized light.

$$E_X = r_X E \cos\phi \quad (5)$$

$$E_Y = r_Y E \sin\phi \quad (6)$$

Then, among the elliptically polarized light, the component perpendicular to the plane of vibration of the incident light passes through the polarized light beam splitter 45 shown in FIG. 12(a) and becomes the polarized light component L4 directed toward the image pickup device 49. The amplitude $E_{L4}$ of the polarized light component L4 is expressed as the following expression (7) using the amplitudes $E_X$ and $E_Y$ in the expressions (5) and (6). By the way, the amplitude $E_C$ of the component parallel to the plane of vibration of the incident light (the component cut by the polarized light beam splitter 45) is expressed by the following expression (8).

$$E_{L4} = E_X \sin\phi + E_Y \cos\phi = 0.5 \, E \, (r_X - r_Y) \sin 2\phi \quad (7)$$

$$E_C = E_X \cos\phi + E_Y \sin\phi = E \, (r_X \cos^2\phi + r_Y \sin^2\phi) \quad (8)$$

Further, the light intensity $I_{L4}$ of the polarized light component L4 having the amplitude $E_{L4}$ in the expression (7) can be expressed by the following expression (9). As can be seen from the expression (9), the light intensity $I_{L4}$ of the polarized light component L4 is the product of the component relating to the form birefringence (the difference $(r_X - r_Y)$ in the amplitude reflectivity) in the case of perpendicular incidence and the component relating to the inclination angle φ (FIG. 14) with respect to the repetition direction of the plane of vibration of the linearly polarized light. Further, when the inclination angle φ of the plane of vibration is constant, the light intensity $I_{L4}$ of the polarized light component L4 depends only on the component relating to the form birefringence (the difference $(r_X - r_Y)$ in the amplitude reflectivity).

$$I_{L4} = (E_{L4})^2 = 0.25 E^2 (r_X - r_Y)^2 \sin^2 2\phi \quad (9)$$

Next, an evaluation on the form birefringence (the difference $(r_X - r_Y)$ in the amplitude reflectivity) in the expression (9) is described. For this evaluation, it is assumed that the substance 1 is a resist (dielectric constant $\epsilon_1 = 2.43$), the substance 2 is air (dielectric constant $\epsilon_2 = 1$), and the thickness $(t_1 + t_2)$ of the layers is 100 nm.

In this case, the substance 1 corresponds to the line portion 2A of the repetitive pattern 22 and the thickness $t_1$ of the substance 1 corresponds to the line width $D_A$ of the line portion 2A (FIG. 3). The substance 2 corresponds to the space portion 2B and the thickness $t_2$ of the substance 2 corresponds to the line width $D_B$ of the space portion 2B. Also, the thickness $(t_1 + t_2)$ of the layers corresponds to the pitch P of the repetitive pattern 22.

Figure 15:
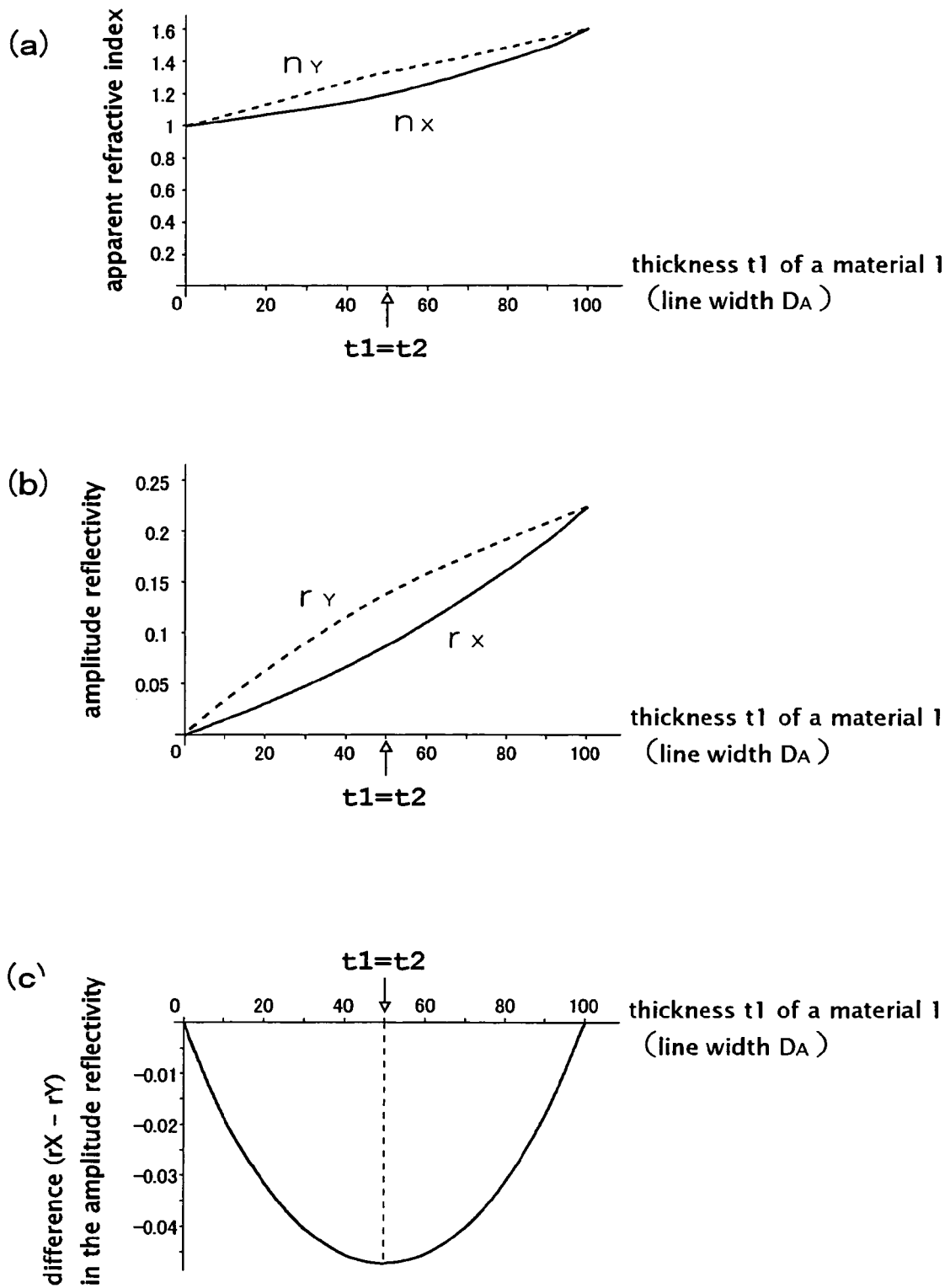
FIGS. 15(a) to 15(c) are diagrams showing a relationship between refractive index (a), amplitude reflectivity (b), and difference in amplitude reflectivity (c) and thickness t1 of a material 1.

The dependence of the apparent refractive index $n_X = \sqrt{\epsilon_X}$ of the polarized light component parallel to the repetition direction of the layer and the apparent refractive index $n_Y = \sqrt{\epsilon_Y}$ of the polarized light component perpendicular to the repetition direction on the thickness $t_1$ of the substance 1 (the line width $D_A$) are shown in FIG. 15(a). Further, the dependence of the amplitude reflectivity $r_X$ of the parallel polarized light component and amplitude reflectivity $r_Y$ of the perpendicular polarized light component on the thickness $t_1$ of the substance 1 (the line width $D_A$) are shown in FIG. 15(b). Furthermore, the relationship between the form birefringence (the difference $(r_X - r_Y)$ in the amplitude reflectivity) and the thickness $t_1$ of the substance 1 (the line width $D_A$) is shown in FIG. 15(c).

As can be seen from FIG. 15(c), when the thickness $t_1$ of the substance 1 is 50 nm, that is, the thickness $t_1$ of the substance 1 is equal to the thickness $t_2$ of the substance 2, the absolute value of the form birefringence (the difference $(r_X - r_Y)$ in the amplitude reflectivity) becomes maximum. Then, as can be seen from the expression (9), when the inclination angle φ of the plane of vibration is constant (45 degrees in the second embodiment), the light intensity $I_{L4}$ of the polarized light component L4 becomes maximum when the form birefringence is maximum, that is, the thickness $t_1$ of the substance 1 is equal to the thickness $t_2$ of the substance 2. Further, when the thickness $t_1$ of the substance 1 changes and the magnitude of the form birefringence in FIG. 15(c) changes, the light intensity $I_{L4}$ of the polarized light component L4 also changes accordingly (refer to FIG. 8).

Therefore, in the surface inspection apparatus 40 in the second embodiment, when the image processing device 15 not shown captures the reflected image of the semiconductor wafer 20 based on the image signal from the image pickup device 49, it compares the brightness information ($\propto$ the light intensity $I_{L4}$ of the polarized light component L4) with the brightness information of the reflected image of the conforming wafer. Then, based on the amount of drop in the brightness value ($\propto$ the amount of drop $\Delta$ in FIG. 8) at a dark portion of the reflected image of the semiconductor wafer 20, defects of the repetitive pattern 22 (the change in the volume ratio between the line portion 2A and the space portion 2B) are detected. For example, it is only necessary to judge that it is "defective" when the amount of drop in the brightness value is larger than a predetermined threshold value and "normal" when it is smaller than the threshold value.

Figure 12:
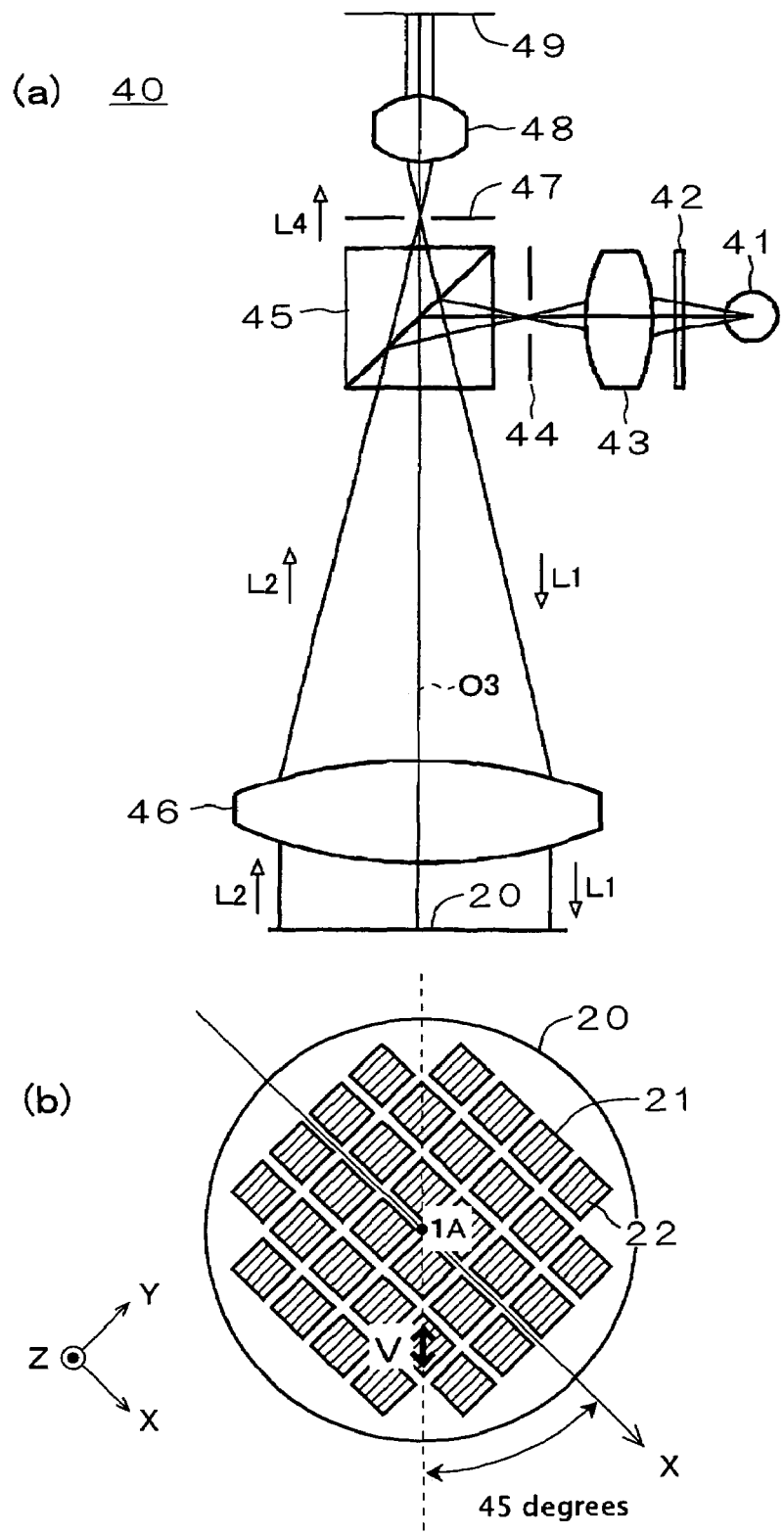
FIGS. 12(a) and 12(b) are diagrams showing an entire configuration of a surface inspection apparatus 40 in a second embodiment.

As described above, according to the surface inspection apparatus 40 in the second embodiment, the repetitive pattern 22 is illuminated using the linearly polarized light L1 in a state in which the direction of the plane of vibration (V direction) in FIG. 12 is inclined with respect to the repetition direction (X direction) of the repetitive pattern 22 and at the same time, defects of the repetitive pattern 22 is detected based on the light intensity $I_{L4}$ of the polarized light component L4 among the elliptically polarized light L2 that has been emitted in the specular direction, therefore, even if the pitch P of the repetitive pattern 22 is sufficiently small compared to the illumination wavelength, it is possible to securely perform a defect inspection. In other words, it is possible to securely cope with reduction of the repetition pitch without the need to shorten the wavelength of the linearly polarized light L1, which is the illumination light.

Figure 16:
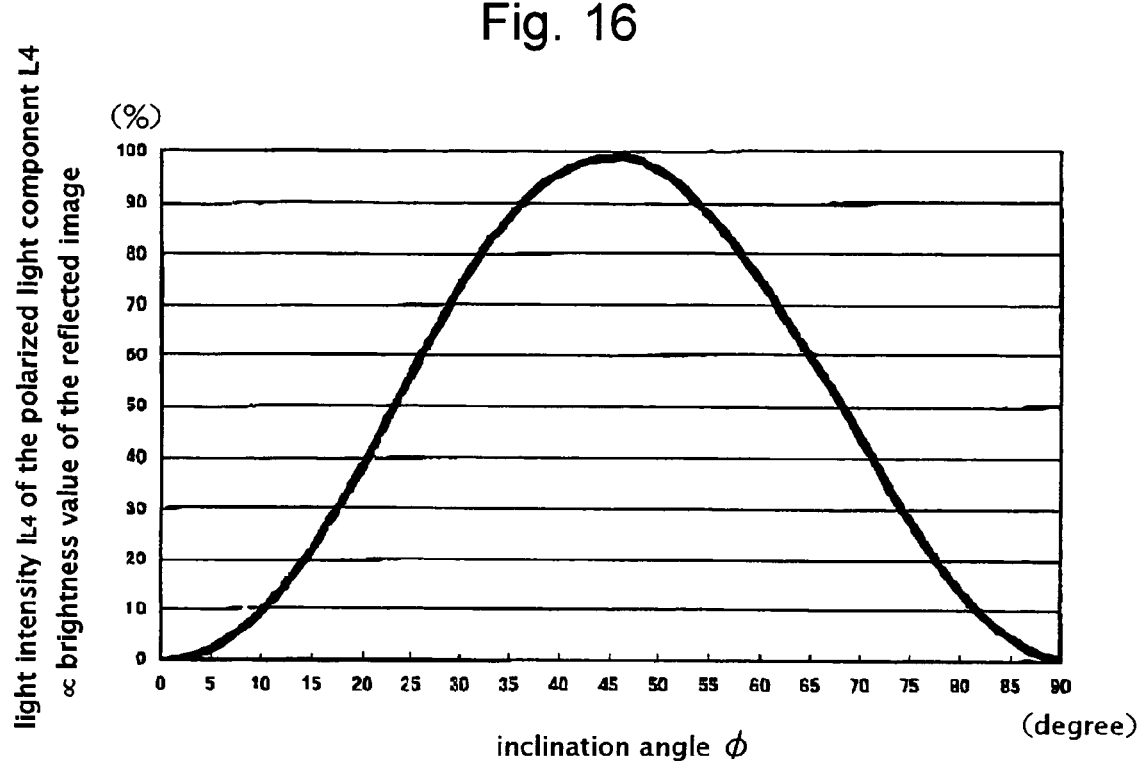
FIG. 16 is a diagram showing a relationship between a light intensity $I_{L4}$ of the polarized light component L4 ($\propto$ brightness value of a reflected image) and the inclination angle $\phi$ (FIG. 14) of the plane of vibration of linearly polarized light.

Further, in the surface inspection apparatus 40 in the second embodiment, the angle formed by the direction (V direction) of the plane of vibration in FIG. 12 and the repetition direction (X direction) is set to 45 degrees, therefore, it is possible to perform a defect inspection of the repetitive pattern 22 with high sensitivity. This point is apparent also from the above-mentioned expression (9). Here, the relationship between the light intensity $I_{L4}$($\propto$ brightness value of the reflected image) and the inclination angle φ (FIG. 14) of the plane of vibration of linearly polarized light in the expression (9) is shown in FIG. 16. It is assumed that the form birefringence ($r_X-r_Y$) is the constant value of the conforming patterns. As can be seen from FIG. 16, the light intensity $I_{L4}$ of the polarized light component L4 takes the maximum value ($=0.25\ E^2\ (r_X-r_Y)^2$) when the inclination angle φ is 45 degrees. Because of this, it is possible to extract the amount of drop in the brightness value of the reflected image of the semiconductor wafer 20 (∝ the amount of drop Δ in FIG. 8) with good sensitivity and a highly sensitive defect inspection becomes possible. Here, the vertical axis in FIG. 16 assumes that the light intensity $I_{L4}$ when the inclination angle φ is 45 degrees (maximum value) is 100%.

Here, the allowable error of the inclination angle φ is considered. In order to detect without fail a line width change of 10% of the line portion 2A of the repetitive pattern 22, it is necessary for the error Δφ of the inclination angle φ to satisfy the following expression (10). The expression (10) is the condition that the amount of change in the light intensity $I_{L4}$ ($\Delta(r_X-r_1)^2$, the amount of drop in the brightness value of the reflected image) resulting from the line width change of 10% exceeds the amount of change in the light intensity $I_{L4}$ ($\sin^2 2\Delta\phi$) resulting from the error Δφ of the inclination angle φ. For example, when the dielectric constant of the resist of the repetitive pattern 22 is 2.43 and the pitch P is 100 nm, in order to detect the line width change of 10% (that is, 5 nm) of the line portion 2A, it is only necessary to suppress the error Δφ of the inclination angle φ below 3.37 degrees.

$$\frac{\Delta(r_X-r_Y)^2}{(r_X-r_Y)^2} \geqq \frac{1-\cos(4\Delta\phi)}{2} \qquad (10)$$

Figure 9:
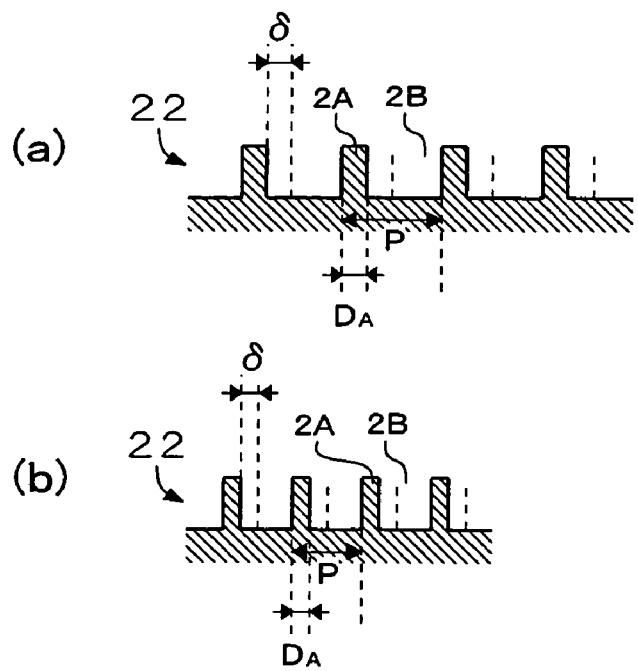
FIGS. 9(a) and 9(b) are diagrams showing an example of the repetitive pattern 22 where a pitch P is different and the volume ratio between the line portion 2A and a space portion 2B is the same.

Moreover, from the surface inspection apparatus 40 in the second embodiment, the following effects [1], [2], and [3] can be obtained, which are the same as those in the above-mentioned first embodiment. [1] Regardless of the pitch P of the repetitive pattern 22, a defect inspection can be performed securely. [2] For example, when the pitches P are different and the volume ratio between the line portion 2A and the space portion 2B is the same, as in the repetitive pattern 22 shown in FIG. 9(a) and FIG. 9(b), a defect inspection can be performed with the same sensitivity. [3] The smaller the pitch P is, the finer change in shape (the amount of deviation δ from the designed value of the line width $D_A$ of the line portion 2A) can be detected securely. These points are apparent from the expression obtained by substituting the expressions (2) and (4) in the above-mentioned expression (9).

Furthermore, from the surface inspection apparatus 40 in the second embodiment, the following effects [4] to [6] can be obtained same as from the above-mentioned first embodiment. [4] The preparation time before a defect inspection actually begins (that is, the time until the reflected image of the semiconductor wafer 20 is captured) can be reduced securely and therefore the operation efficiency is improved. [5] The stage 11 does not have the tilt mechanism and the light source 41 is an inexpensive discharge light source, therefore, the apparatus configuration is simplified. [6] Even when repetitive patterns different in the pitch P and in the repetition direction (X direction) are present mixedly, a defect inspection of all of the repetitive patterns can be performed totally and simply.

Third Embodiment

In the configuration in the first embodiment, the light detecting system 14 obtains the image signal by condensing the reflected light from the wafer 20 into an image on the image pickup plane of the image pickup device 39 thereby a defect inspection is performed, however, in the present embodiment, an observer performs an inspection visually by seeing the reflected light from the wafer 20 with his/her eyes.

Figure 17:
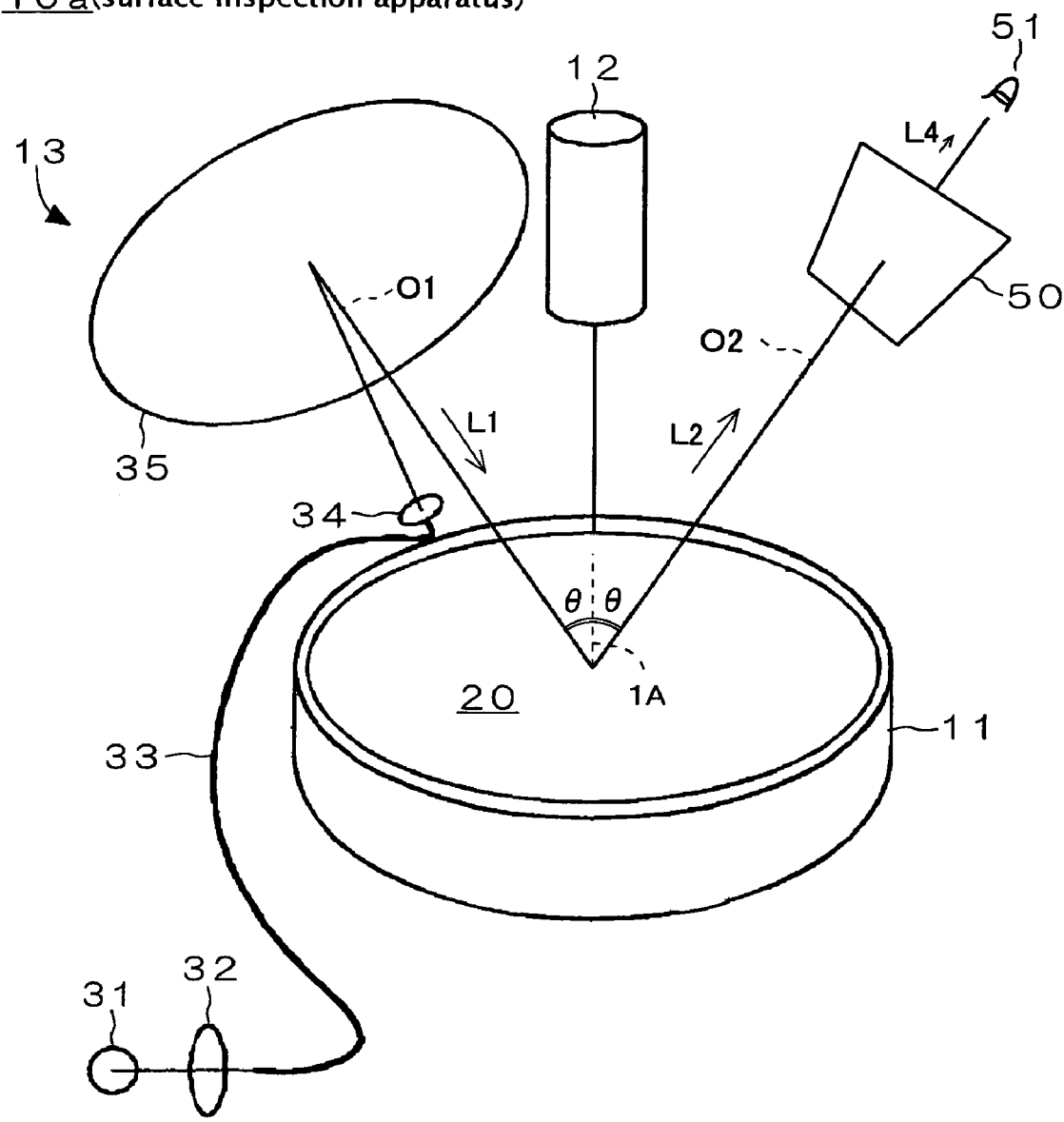
FIG. 17 is a diagram showing an entire configuration of a surface inspection apparatus 10a in a third embodiment.

FIG. 17 is a diagram showing the configuration of a surface inspection apparatus 10a according to the third embodiment. In FIG. 17, the members with the same symbols as those in FIG. 1 are the same members as those in FIG. 1. In other words, the configuration of the stage 11 and the illumination system 13 is the same as that in FIG. 1 (the first embodiment). Then, as in the first embodiment, the repetition direction (X direction) of the repetitive pattern 22 of the semiconductor wafer 20 is set to an angle of 45 degrees with respect to the incident plane (3A) of the linearly polarized light L1.

A polarization filter 50 is arranged on the optical path of the elliptically polarized light L2 from the repetitive pattern 22 on the semiconductor wafer 20. The orientation of the transmission axis of the polarization filter 50 is set so as to be perpendicular to the transmission axis of the polarization filter 34 in the illumination system 13 (the cross Nicol state), as in the polarization filter 38 in the first embodiment. Therefore, it is possible to extract only the polarized light component L4 corresponding to the polarized light component L3 in FIG. 5(c) of the elliptically polarized light L2. The polarized light component L4 thus extracted enters eyes 51 of an observer and is observed by the observer.

Incidentally, it is preferable for the polarization filter 50 to have a size with which the entire image of the semiconductor wafer 20 can be seen through the polarization filter 50 by the observer.

The observer checks the brightness at each portion of the image of the semiconductor wafer 20 through the polarization filter 50 and detects defects of the repetitive pattern 22 based on the amount of drop in the brightness.

According to the third embodiment described above, the same effects as those described in the first embodiment can be obtained.

MODIFICATION EXAMPLES

By the way, in the embodiments described above, the angle (the inclination angle φ in FIG. 14) formed by the direction of the plane of vibration (V direction) of the linearly polarized light L1 on the surface of the semiconductor wafer 20 and the repetition direction (X direction) of the repetitive pattern 22 is set to 45 degrees, however, the present invention is not limited to this. As can be seen from FIG. 16 already described, when the inclination angle φ is set to 45 degrees±15 degrees, the brightness drops by about 70% and when 45 degrees±20 degrees, the brightness drops by about 55%. In other words, when the inclination angle φ is in a range from 30 degrees to 60 degrees, more than 70% of the brightness value when the angle is set to 45 degrees can be secured, therefore, it is possible to perform the same defect inspection as that described above. Further, the rate of drop in the brightness value due to the change in shape at the time of defocus (for example, 50% etc.) is constant regardless of the inclination angle φ. Therefore, the amount of drop in the brightness value at the time of defocus (the difference in the brightness from that at the time of focus) becomes smaller as the inclination angle φ further deviates from 45 degrees. However, if the inclination angle φ is in a range from 30 degrees to 60 degrees, an inspection can be performed sufficiently. In an actual operation, it is much preferable for the inclination angle φ to be in a range from 35 degrees to 55 degrees.

Moreover, the embodiments above has described a case in which the amount of drop in the brightness value of the reflected image of the semiconductor wafer 20 is obtained using the brightness value of the reflected image of the conforming wafer as a reference, to detect a detect of the repetitive pattern 22, however, the present invention is not limited thereto. Since the arrangement of the repetitive patterns in each chip region 21 (FIG. 2) of the semiconductor wafer 20 is the same, it may also be possible to identify the chip region of the conforming product or the shot region of the conforming product and perform a defect inspection with the brightness value as a reference. In this case, it is no longer necessary to manufacture a dedicated wafer the entire surface of which is conforming. In addition, it may also be possible to compare with the brightness value of a limit sample. Further, it may also be possible to determine the reference of the brightness value by simulation and perform a defect detection of the repetitive pattern 22 by comparison with the reference value.

Furthermore the embodiments above has described a case where the designed value of the line width $D_A$ of the line portion 2A of the repetitive pattern 22 is set to ½ of the pitch P (the ideal volume ratio between the line portion 2A and the space portion 2B is set to 1:1), however, the present invention is not limited thereto. The present invention is applicable when the ideal volume ratio is not 1:1. In this case, the brightness value of the reflected image of the semiconductor wafer 20 may increase depending on the change in shape of the repetitive pattern 22.

In addition, the embodiments above has described a case where the semiconductor wafer 20 is a substrate to be inspected, however, the present invention is not limited thereto. The present invention can be applied to defect inspection on a liquid crystal substrate (a substrate to be inspected) in the production process of a liquid crystal display device. Further, the same effects is obtainable not only in defect detection processing by the image processing device 15 of the surface inspection apparatus, but also in that by an external computer connected to the surface inspection apparatus.

Further, the embodiments above have employed a two-dimensional sensor such as a CCD as the image pickup device 39, however, a one-dimensional sensor may be used. In this case, the entire image of a semiconductor wafer (or a liquid crystal substrate) may be captured by relatively moving the one-dimensional sensor an image pickup device and a stage that mounts thereon the semiconductor wafer (or the liquid crystal substrate) as a substrate to be inspected, and causing the one-dimensional sensor to scan the entire surface of the semiconductor wafer (or the liquid crystal substrate).

The invention is not limited to the above embodiments and various modifications may be made without departing from the spirit and scope of the invention. Any improvement may be made in part or all of the components.

What is claimed is:

1. A surface inspection apparatus comprising:
    an illumination unit which illuminates a surface of a substrate to be inspected with linearly polarized light;
    a setting unit which sets a direction of a vibration plane of said linearly polarized light on the surface of the substrate to be inspected such that the direction of the vibration plane is neither parallel to nor orthogonal to a repetition direction of repetitive pattern(s) formed on said surface;
    an imaging unit which captures an image of the surface of the substrate to be inspected, using a polarized light component of light that has been reflected from said repetitive pattern(s), to generate image data for two different directions, the polarized light component being perpendicular to the vibration plane of said linearly polarized light; and
    a detection unit which detects a defect of said repetitive pattern(s) according to said image data.

2. The surface inspection apparatus according to claim 1, wherein
    a detection unit detects a defect of said repetitive pattern(s) by comparing image data on a conforming substrate stored in advance and the image data generated by said imaging unit, the conforming substrate having ideal repetitive patterns formed thereon.

3. The surface inspection apparatus according to claim 1, wherein
    a detection unit determines a region of said image data as a defect when a brightness value of the region is smaller than a predetermined threshold value.

4. The surface inspection apparatus according to claim 1, wherein
    said setting unit sets an angle between the direction of the vibration plane of said linearly polarized light on the surface of the substrate to be inspected and the repetition direction of the repetitive pattern(s) formed on said surface to an arbitrary value between 30 degrees and 60 degrees.

5. The surface inspection apparatus according to claim 1, wherein
    said setting unit sets the angle between the direction of the vibration plane of said linearly polarized light on the surface of the substrate to be inspected and the repetition direction of the repetitive pattern(s) formed on said surface to 45 degrees.

6. The surface inspection apparatus according to claim 1, wherein:
    said setting unit sets the direction of the vibration plane of said linearly polarized light on the surface of the substrate to be inspected and the repetition direction of the repetitive pattern(s) formed on said surface to be diagonal, by supporting said substrate to be inspected and rotating said substrate to be inspected within said surface; and
    said detection unit detects a defect of said repetitive pattern(s) according to a state in which said substrate is before and after said setting unit rotates the repetition direction by 180 degrees.

7. A surface inspection method comprising the steps of:
    illuminating, with linearly polarized light, repetitive pattern(s) formed on a surface of a substrate to be inspected in a state in which a direction of a vibration plane of the linearly polarized light on the surface is neither parallel to nor orthogonal to a repetition direction of said repetitive pattern(s);
    capturing an image of the surface of the substrate to be inspected using a polarized light component of light that has been reflected from said repetitive pattern(s), to generate image data for two different directions, the polarized light component being perpendicular to the vibration plane of said linearly polarized light; and detecting a defect of said repetitive pattern(s) according to the image data.

8. The surface inspection method according to claim 7, wherein
the direction of the vibration plane of said linearly polarized light on said surface is inclined at an arbitrary angle between 30 degrees and 60 degrees with respect to a repetition direction of said repetitive pattern(s).

9. The surface inspection method according to claim 7, wherein
the direction of the vibration plane of said linearly polarized light on said surface is inclined at 45 degrees with respect to a repetition direction of said repetitive pattern(s).

10. The surface inspection method according to claim 7, wherein
a defect of said repetitive pattern(s) is detected in a state in which said substrate to be inspected is in before and after the repetition direction of said repetitive pattern(s) is rotated by 180 degrees within said surface.

11. The surface inspection method according to claim 7, wherein
the defect of said repetitive pattern(s) is detected by comparing image data on a conforming substrate stored in advance and the generated image data, the conforming substrate having ideal repetitive patterns formed thereon.

12. The surface inspection method according to claim 7, wherein
the detection of the defect of said repetitive pattern(s) is performed by determining a region of said image data as the defect when a brightness value of the region is smaller than a predetermined threshold value.

13. The surface inspection method according to claim 11, wherein
the defect of said repetitive pattern(s) is detected according to a drop in the brightness value of the image data relative to that of the image data on the conforming substrate.

14. The surface inspection apparatus according to claim 2, wherein
said detection unit detects the defect of said repetitive pattern(s) according to a drop in the brightness value of the image data relative to that of the image data on the conforming substrate.

* * * * *